(12) United States Patent
Olson et al.

(10) Patent No.: US 11,747,900 B2
(45) Date of Patent: *Sep. 5, 2023

(54) EYE-TRACKING IMAGE VIEWER FOR DIGITAL PATHOLOGY

(71) Applicant: Leica Biosystems Imaging, Inc., Vista, CA (US)

(72) Inventors: Allen Olson, San Diego, CA (US); Kiran Saligrama, San Diego, CA (US)

(73) Assignee: Leica Biosystems Imaging, Inc., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/859,765

(22) Filed: Jul. 7, 2022

(65) Prior Publication Data

US 2022/0342479 A1    Oct. 27, 2022

Related U.S. Application Data

(63) Continuation of application No. 17/281,907, filed as application No. PCT/US2019/067665 on Dec. 19, 2019, now Pat. No. 11,385,713.

(60) Provisional application No. 62/782,191, filed on Dec. 19, 2018.

(51) Int. Cl.
| | | |
|---|---|---|
| *G06V 40/18* | (2022.01) | |
| *G06F 3/01* | (2006.01) | |
| *G16H 40/67* | (2018.01) | |
| *G16H 30/20* | (2018.01) | |

(Continued)

(52) U.S. Cl.
CPC .............. *G06F 3/013* (2013.01); *G06F 3/017* (2013.01); *G06F 3/0485* (2013.01); *G06V 40/18* (2022.01); *G16H 30/20* (2018.01); *G16H 40/67* (2018.01); *G16H 50/20* (2018.01)

(58) Field of Classification Search
CPC ......... G06F 3/013; G16H 40/67; G16H 30/20
See application file for complete search history.

(56) References Cited

U.S. PATENT DOCUMENTS

| | | | |
|---|---|---|---|
| 11,385,713 B2* | 7/2022 | Olson | .................... G06F 3/0485 |
| 2002/0105482 A1* | 8/2002 | Lemelson | ............... G06F 3/013 |
| | | | 345/32 |
| 2011/0060766 A1 | 3/2011 | Ehlke et al. | |

(Continued)

OTHER PUBLICATIONS

Adams, Nicholas, Mark Witkowski, and Robert Spence. "The inspection of very large images by eye-gaze control." *Proceedings of the working conference on Advanced visual interfaces*. 2008.

(Continued)

*Primary Examiner* — Edward Park
(74) *Attorney, Agent, or Firm* — Frost Brown Todd LLP

(57) ABSTRACT

Image viewing in digital pathology using eye-tracking. In an embodiment, a position of a user's gaze on a graphical user interface, comprising at least a portion of a digital slide image within a macro view, is repeatedly detected based on an output from an eye-tracking device. After detecting a change of the user's gaze from a first position to a second position on the graphical user interface, a view of the digital slide image within the macro view is automatically panned based on the second position, so as to move a position on the digital slide image that corresponds to the second position on the graphical user interface toward a center of the macro view.

20 Claims, 3 Drawing Sheets

(51) Int. Cl.
  *G06F 3/0485*  (2022.01)
  *G16H 50/20*  (2018.01)

(56) References Cited

U.S. PATENT DOCUMENTS

| | | | |
|---|---|---|---|
| 2014/0365936 A1* | 12/2014 | Kim | G06F 3/0482 715/838 |
| 2015/0082136 A1 | 3/2015 | Cameron et al. | |
| 2018/0181272 A1 | 6/2018 | Olsson et al. | |
| 2018/0324414 A1 | 11/2018 | Hoffman et al. | |
| 2022/0019281 A1 | 1/2022 | Olson et al. | |

OTHER PUBLICATIONS

Leargningtofly: "javascript—Pan Larger image when Thumbnail is panned—Stack Overflow", Jan. 26, 2013, 1 page. Retrieved on Apr. 13, 2022, from https://stackoverflow.com/questions/14532681/pan-larger-image-when-thumbnail-is-panned.

Shin, Dmitriy, et al. "PathEdEx—Uncovering high-explanatory visual diagnostics heuristics using digital pathology and multiscale gaze data." *Journal of Pathology Informatics* 8.1 (2017): 29.

Stellmach, Sophie, and Raimund Dachselt. "Investigating gaze-supported multimodal pan and zoom." *Proceedings of the Symposium on Eye Tracking Research and Applications*. 2012.

Supplemental European Search Report dated Apr. 26, 2022, for Application No. 19899957.5, 8 pages.

Invitation to Pay Additional Fees and, Where Applicable, Protest Fee dated Feb. 6, 2020, for International Application No. PCT/US2019/067665, 2 pages.

International Search Report and Written Opinion dated Apr. 14, 2020, for International Application No. PCT/US2019/067665, 17 pages.

International Preliminary Report on Patentability dated Feb. 17, 2021, for International Application No. PCT/US2019/067665, 25 pages.

* cited by examiner

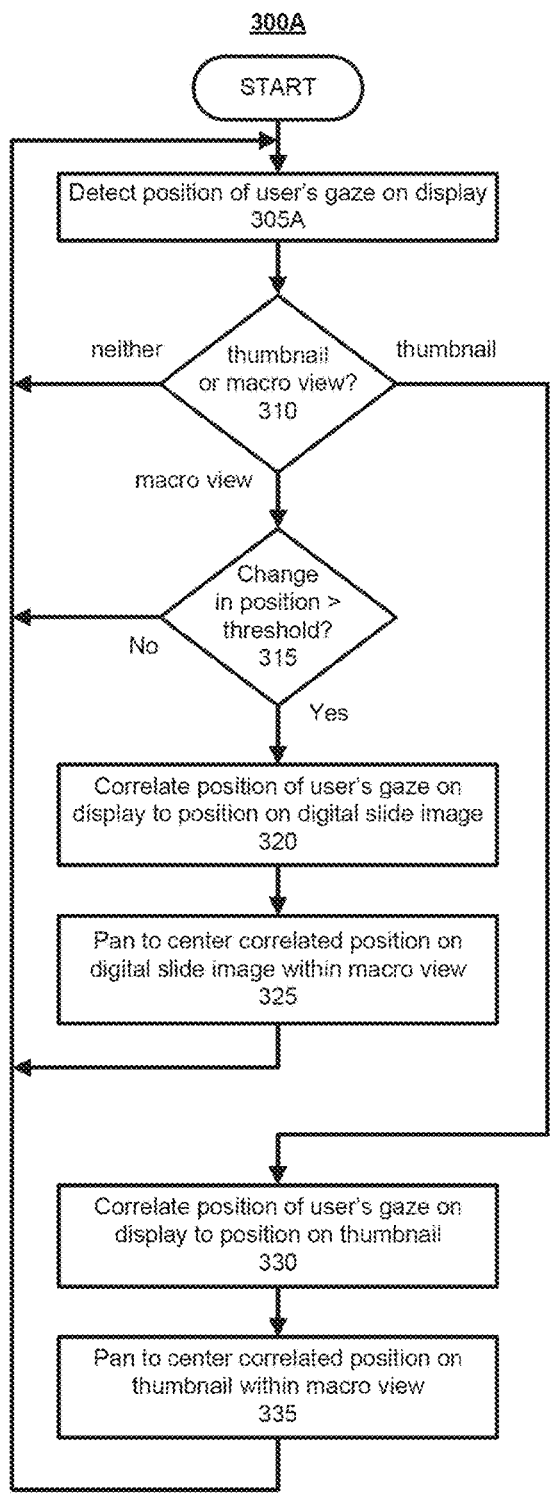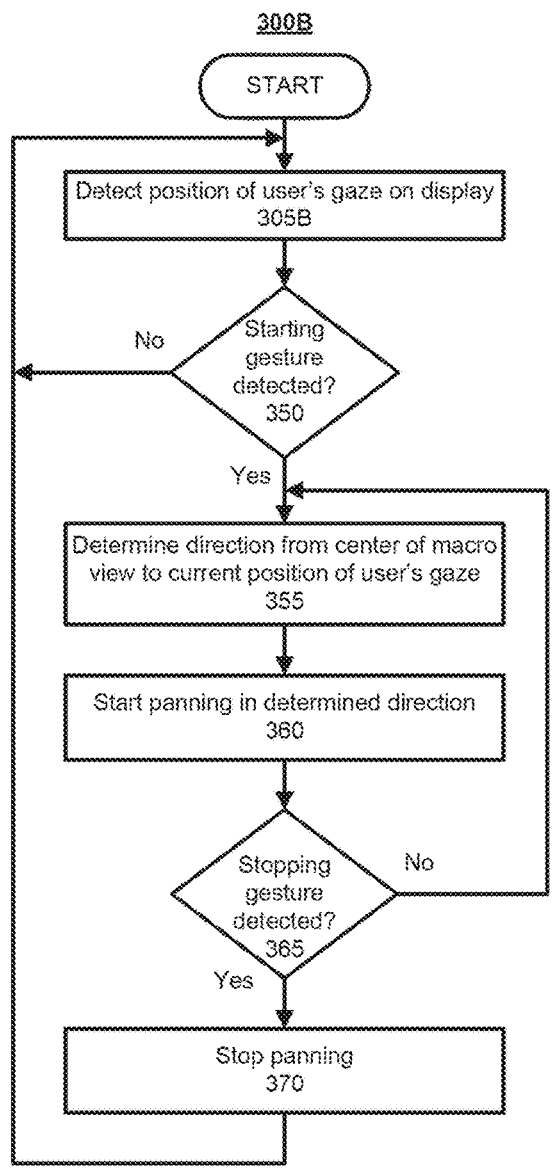
FIG. 3A
FIG. 3B

EYE-TRACKING IMAGE VIEWER FOR DIGITAL PATHOLOGY

CROSS-REFERENCE TO RELATED APPLICATIONS

The present application claims priority to U.S. Provisional Patent App. No. 62/782,191, filed on Dec. 19, 2018, which is hereby incorporated herein by reference as if set forth in full.

BACKGROUND

Field of the Invention

The embodiments described herein are generally directed to digital pathology, and, more particularly, to the use of eye-tracking during the viewing of digital pathology slide images.

Description of the Related Art

In digital pathology, microscope slides are scanned at very high resolutions to obtain very high-resolution digital slide images. A digital slide image is typically viewed on a computer display by a pathologist. Typically, the pathologist uses a keyboard, mouse, trackball, touchpad or other touch sensor, or other hand-operated input device to navigate between regions of the digital slide image on the display. In addition, since the number of pixels in the digital slide image is generally much larger than the pixels in the display (e.g., gigapixels in the image v. megapixels in the display), only a region of the digital slide image may be viewable at high resolution (e.g., native resolution) at a time. Thus, the pathologist must also use the hand-operated input device to zoom in, zoom out, and pan the digital slide image being displayed, in order to view a region of interest within the digital slide image at high magnification.

Using a mouse as an example of the hand-operated input device, the pathologist may perform a mouse click on an area of the digital slide image and then use a mouse scroll (e.g., via a scroll wheel on the mouse) to zoom in (increase magnification) or zoom out (decrease magnification) from the current magnification. To pan to a new region of the digital slide image, the pathologist may perform a mouse drag (e.g., by pressing and holding the mouse button while moving the mouse) to center the view of the digital slide image on another region of the digital slide image. The pathologist may also be required to use other mouse operations, such as a mouse click on a thumbnail of the digital slide image to move a view of the digital slide image from one region to a new region of the digital slide image, a mouse click or mouse drag to operate an input (e.g., button, slider, etc.) to change a magnification of the view of the digital slide image (e.g., to zoom in or zoom out, select a preset magnification, etc.), and/or the like. In some cases, the pathologist may also use keyboard shortcuts to perform the same or similar operations.

Regardless of the particular hand-operated input device that is used, the amount of hand activity required to view the digital slide image is quite large. Consequently, pathologists spend a significant amount of time reviewing digital slide images in this manner. The use of such hand-operated input devices is tedious, cumbersome, time consuming, and can lead to repetitive-motion pain or injury.

SUMMARY

Accordingly, systems, methods, and non-transitory computer-readable media are disclosed for utilizing an eye-tracking device to review digital slide images. The eye-tracking device may be mounted on a computer display or integrated into the computer display or may be mounted on or integrated into gear worn by the user (e.g., ordinary glasses, smart glasses, virtual reality (VR) headset, etc.), and may be configured to detect the position of a user's gaze on the computer display in real time. Advantageously, functions can be executed, based on the outputs of the eye-tracking device, to replace one or more, including potentially all, viewing-related functions currently performed by hand-operated input devices (e.g., mouse, keyboard, touch sensor, etc.), thereby reducing or eliminating the need for the hand-operated input devices during the review of digital slide images (e.g., in digital pathology).

In an embodiment, a method is disclosed that comprises using at least one hardware processor to: repeatedly detect a position of a user's gaze on a graphical user interface based on an output from an eye-tracking device, wherein the graphical user interface comprises at least a portion of a digital slide image within a macro view; and, after detecting a change of the user's gaze from a first position to a second position on the graphical user interface, automatically pan a view of the digital slide image within the macro view based on the second position, so as to move a position on the digital slide image that corresponds to the second position on the graphical user interface toward a center of the macro view. The automatic panning may be performed in response to detecting that a distance between the first position and the second position is greater than a threshold value. The threshold value may be greater than zero. The method may further comprise using the at least one hardware processor to automatically pan the view until the position on the digital slide image that corresponded to the second position on the graphical user interface is within the center of the macro view. The method may further comprise using the at least one hardware processor to automatically pan the view until the detected position of the user's gaze is within the center of the macro view. The method may further comprise using the at least one hardware processor to: detect an orientation of the user's head based on the output from the eye-tracking device; and detect a predetermined starting gesture based on one or more detected orientations of the user's head, wherein the automatic panning is performed in response to detecting the predetermined starting gesture. The method may further comprise using the at least one hardware processor to: detect a predetermined stopping gesture based on one or more detected orientations of the user's head; and, in response to detecting the predetermined stopping gesture, automatically stop the panning of the view of the digital slide image within the macro view. The graphical user interface may comprise a thumbnail image of the digital slide image, and the method may further comprise using the at least one hardware processor to: determine whether or not the detected position of the user's gaze is within the thumbnail image; and, in response to detecting that the position of the user's gaze is within the thumbnail image, determine a position on the digital slide image that corresponds to the position within the thumbnail image, and update the macro view such that the determined position on the digital slide image is within the center of the macro view. Updating the macro view may comprise automatically panning the view of the digital slide image, so as to move the determined position on the digital slide image to the center of the macro view. The method may further comprise using the at least one hardware processor to calculate a distance between the first position and the second position, wherein a speed of the automatic panning is based on the calculated distance.

In an embodiment, a method is disclosed that comprises using at least one hardware processor to: repeatedly detect a position of a user's gaze on a graphical user interface based on an output from an eye-tracking device, wherein the graphical user interface comprises at least one or more inputs and a portion of a digital slide image within a macro view; and, when detecting that the position of the user's gaze is within one of the one or more inputs, detect an orientation of the user's head, from among a plurality of possible orientations, based on the output from the eye-tracking device, identify a function associated in memory with the one input and the detected orientation, and, based on detecting the orientation associated with the identified function, start the function. The function may comprise changing a magnification level of the digital slide image within the macro view. The one input may comprise an input for changing a magnification level of the digital slide image within the macro view, wherein the plurality of possible orientations comprise a first orientation and a second orientation, wherein the first orientation is associated in the memory with a function of increasing the magnification level, and wherein the second orientation is associated in the memory with a function of decreasing the magnification level. The first orientation may comprise a head tilt in a first direction, and the second orientation may comprise a head tilt in a second direction that is opposite the first direction. The method may further comprise, after starting the function, when detecting that the position of the user's gaze is no longer within the one input, stopping the function.

In an embodiment, a method is disclosed that comprises using at least one hardware processor to: repeatedly detect a position of a user's gaze on a graphical user interface based on an output from an eye-tracking device, wherein the graphical user interface comprises at least one or more inputs and a portion of a digital slide image within a macro view; and, when detecting that the position of the user's gaze is within one of the one or more inputs, detect an orientation of the user's head based on the output from the eye-tracking device, detect a predetermined starting gesture based on one or more detected orientations of the user's head, and, based on detecting the predetermined starting gesture, start a function associated with the one input. The function may comprise changing a magnification level of the digital slide image within the macro view. The method may further comprise, after starting the function, when detecting that the position of the user's gaze is no longer within the one input, stopping the function. The predetermined starting gesture may comprise a repetitive movement of the user's head. The one or more inputs may comprise a plurality of inputs that are each associated with a different function than any other one of the plurality of inputs, wherein the predetermined starting gesture is identical for each of the plurality of inputs.

In an embodiment, a method is disclosed that comprises using at least one hardware processor to: for one or more first digital slide images, repeatedly detect a position of a user's gaze on a graphical user interface and head orientation based on an output from an eye-tracking device, wherein the graphical user interface comprises at least a portion of the first digital slide image within a macro view, and store a viewing history comprising each detected position of the user's gaze and head orientation in association with a portion of the first digital slide image being viewed when the user's gaze or head orientation was detected; based on the viewing history stored for the one or more first digital slide images, train a machine-learning algorithm to predict a next portion of at least one second digital slide image to be viewed by the user; use the trained machine-learning algorithm to predict the next portion of the at least one second digital slide image to be viewed by the user based on past portions of the at least one second digital slide image that have been viewed by the user; and automatically pan to the next portion of the at least one second digital slide image to be viewed, as predicted by the trained machine-learning algorithm, without user intervention.

Any of the disclosed methods may be embodied in executable software modules of a processor-based system, such as a server, and/or in executable instructions stored in a non-transitory computer-readable medium.

BRIEF DESCRIPTION OF THE DRAWINGS

The details of the present invention, both as to its structure and operation, may be gleaned in part by study of the accompanying drawings, in which like reference numerals refer to like parts, and in which:

FIGS. 3A and 3B illustrate example processes for panning a digital slide image using the output of an eye-tracking device, according to embodiments.

DETAILED DESCRIPTION

In an embodiment, systems, methods, and non-transitory computer-readable media are disclosed for utilizing an eye-tracking device to review digital slide images. After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. System Overview 1.1. Example Processing Device

Figure 1:
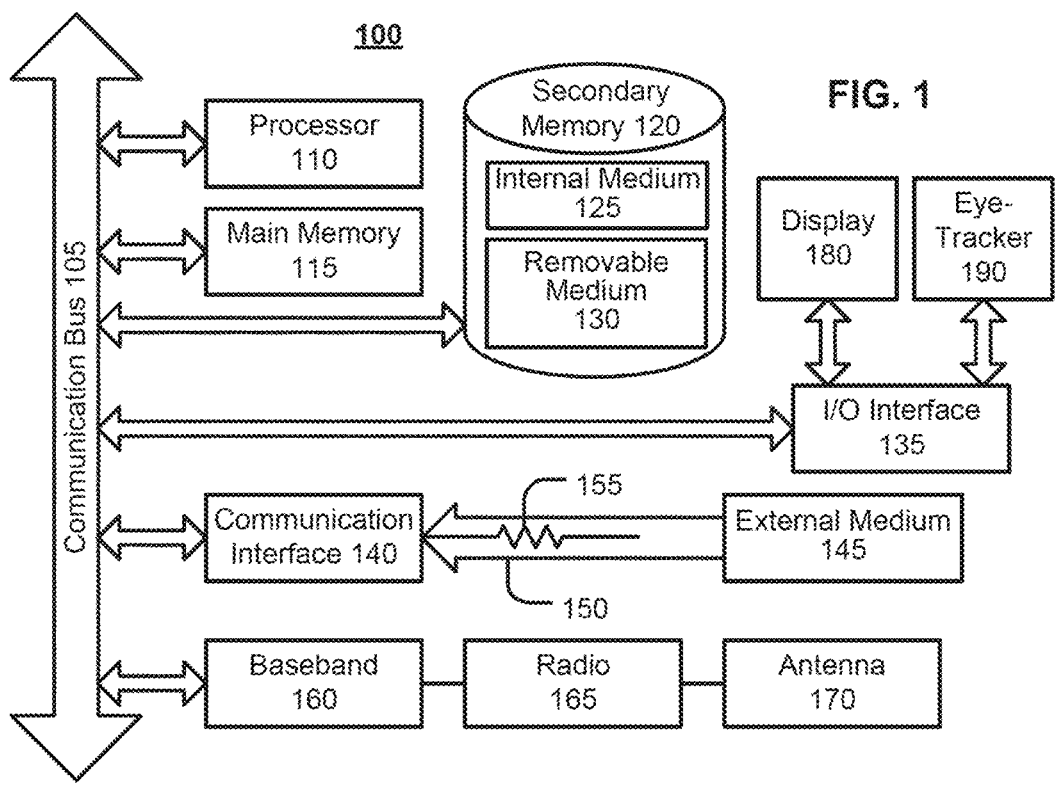
FIG. 1 illustrates an example processing system, by which one or more of the processed described herein, may be executed, according to an embodiment.

FIG. 1 is a block diagram illustrating an example wired or wireless system 100 that may be used in connection with various embodiments described herein. For example, system 100 may be used as or in conjunction with one or more of the functions, processes, or methods (e.g., to store and/or execute an application or one or more software modules of an application) described herein. System 100 can be a server, personal computer, digital slide scanning apparatus, or any other processor-enabled device that is capable of wired or wireless data communication. Other computer systems and/or architectures may be also used, as will be clear to those skilled in the art.

System 100 preferably includes one or more processors, such as processor 110, which may comprise a central processing unit (CPU). Additional processors may be provided, such as a graphics processing unit (GPU), an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 110. Examples of processors which may be used with system 100 include, without limitation, the Pentium® processor, Core i7® processor, and Xeon® processor, all of which are available from Intel Corporation of Santa Clara, Calif.

Processor 110 is preferably connected to a communication bus 105. Communication bus 105 may include a data channel for facilitating information transfer between storage and other peripheral components of system 100. Furthermore, communication bus 105 may provide a set of signals used for communication with processor 110, including a data bus, address bus, and/or control bus (not shown). Communication bus 105 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 100 preferably includes a main memory 115 and may also include a secondary memory 120. Main memory 115 provides storage of instructions and data for programs executing on processor 110, such as one or more of the functions and/or modules discussed herein. It should be understood that programs stored in the memory and executed by processor 110 may be written and/or compiled according to any suitable language, including without limitation C/C++, Java, JavaScript, Perl, Visual Basic, .NET, and the like. Main memory 115 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 120 may optionally include an internal medium 125 and/or a removable medium 130. Removable medium 130 is read from and/or written to in any well-known manner. Removable storage medium 130 may be, for example, a magnetic tape drive, a compact disc (CD) drive, a digital versatile disc (DVD) drive, other optical drive, a flash memory drive, and/or the like.

Secondary memory 120 is a non-transitory computer-readable medium having computer-executable code (e.g., disclosed software modules) and/or other data stored thereon. The computer software or data stored on secondary memory 120 is read into main memory 115 for execution by processor 110.

In alternative embodiments, secondary memory 120 may include other similar means for allowing computer programs or other data or instructions to be loaded into system 100. Such means may include, for example, a communication interface 140, which allows software and data to be transferred from external storage medium 145 to system 100. Examples of external storage medium 145 may include an external hard disk drive, an external optical drive, an external magneto-optical drive, and/or the like. Other examples of secondary memory 120 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 100 may include a communication interface 140. Communication interface 140 allows software and data to be transferred between system 100 and external devices (e.g. printers), networks, or other information sources. For example, computer software or executable code may be transferred to system 100 from a network server via communication interface 140. Examples of communication interface 140 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 100 with a network or another computing device. Communication interface 140 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 140 are generally in the form of electrical communication signals 155. These signals 155 may be provided to communication interface 140 via a communication channel 150. In an embodiment, communication channel 150 may be a wired or wireless network, or any variety of other communication links. Communication channel 150 carries signals 155 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed software modules) is stored in main memory 115 and/or secondary memory 120. Computer programs can also be received via communication interface 140 and stored in main memory 115 and/or secondary memory 120. Such computer programs, when executed, enable system 100 to perform the various functions of the disclosed embodiments as described elsewhere herein.

In this description, the term "computer-readable medium" is used to refer to any non-transitory computer-readable storage media used to provide computer-executable code and/or other data to or within system 100. Examples of such media include main memory 115, secondary memory 120 (including internal memory 125, removable medium 130, and external storage medium 145), and any peripheral device communicatively coupled with communication interface 140 (including a network information server or other network device). These non-transitory computer-readable media are means for providing executable code, programming instructions, software, and/or other data to system 100.

In an embodiment that is implemented using software, the software may be stored on a computer-readable medium and loaded into system 100 by way of removable medium 130, I/O interface 135, or communication interface 140. In such an embodiment, the software is loaded into system 100 in the form of electrical communication signals 155. The software, when executed by processor 110, preferably causes processor 110 to perform one or more of the processes and functions described elsewhere herein.

In an embodiment, I/O interface 135 provides an interface between one or more components of system 100 and one or more input and/or output devices. Example input devices include, without limitation, eye-tracking devices, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), wearable devices (e.g., smart glasses, VR headset, etc.), and/or the like. In some cases, an input and output device may be combined, such as in the case of a touch panel display (e.g., in a smartphone, tablet, or other mobile device).

In the illustrated embodiment, I/O interface 135 interfaces with at least a display 180 and an eye-tracking device 190, such that processor 110 can render data to be displayed on display 180 and receive data sensed by eye-tracking device 190. The data sensed by eye-tracking device 190 may indicate a gaze position on display 180 at which the eyes of a user of system 100 are currently directed and may be repeatedly received by processor 110 (e.g., at regular intervals and/or whenever the gaze position changes). In an embodiment, display 180 and eye-tracking device 190 may be integrated into a single device, such as a computer monitor, smart glasses, a VR headset, and/or the like.

System 100 may also include optional wireless communication components that facilitate wireless communication over a voice network and/or a data network. The wireless communication components comprise an antenna system 170, a radio system 165, and a baseband system 160. In system 100, radio frequency (RF) signals are transmitted and received over the air by antenna system 170 under the management of radio system 165.

In an embodiment, antenna system 170 may comprise one or more antennae and one or more multiplexors (not shown) that perform a switching function to provide antenna system 170 with transmit and receive signal paths In the receive path, received RF signals can be coupled from a multiplexor to a low noise amplifier (not shown) that amplifies the received RF signal and sends the amplified signal to radio system 165.

In an alternative embodiment, radio system 165 may comprise one or more radios that are configured to communicate over various frequencies. In an embodiment, radio system 165 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 165 to baseband system 160.

If the received signal contains audio information, then baseband system 160 decodes the signal and converts it to an analog signal. Then the signal is amplified and sent to a speaker. Baseband system 160 also receives analog audio signals from a microphone. These analog audio signals are converted to digital signals and encoded by baseband system 160. Baseband system 160 also encodes the digital signals for transmission and generates a baseband transmit audio signal that is routed to the modulator portion of radio system 165. The modulator mixes the baseband transmit audio signal with an RF carrier signal, generating an RF transmit signal that is routed to antenna system 170 and may pass through a power amplifier (not shown). The power amplifier amplifies the RF transmit signal and routes it to antenna system 170, where the signal is switched to the antenna port for transmission.

Baseband system 160 is also communicatively coupled with processor 110. Processor 110 has access to data storage areas 115 and 120. Processor 110 is preferably configured to execute instructions (i.e., computer programs, such as the disclosed application, or software modules) that can be stored in main memory 115 or secondary memory 120. Computer programs can also be received from baseband processor 160 and stored in main memory 110 or in secondary memory 120, or executed upon receipt. Such computer programs, when executed, enable system 100 to perform the various functions of the disclosed embodiments.

1.2. Eye-Tracking Device

As discussed above, in an embodiment, system 100 comprises an eye-tracking device 190. Eye-tracking device 190 may be mounted on display 180 or integrated into display 180. In an embodiment, eye-tracking device 190 and display 180 may be integrated into a single device, such as a computer monitor, smart glasses, VR headset, and/or the like. Alternatively, eye-tracking device 190 may be separate from display 180. In any case, eye-tracking device 190 should be mounted or otherwise positioned to detect a user's gaze with respect to display 180.

In an embodiment, eye-tracking device 190 may be dedicated to tracking a user's gaze. Alternatively, eye-tracking device 190 could comprise a camera (e.g., mounted on or integrated into display 180) which is also used for more conventional imaging, such as capturing photographs or video of a user of system 100 (e.g., for social media, a webcam, video conferencing, etc.).

Eye-tracking device 190 may comprise any consumer-grade, commercial off-the-shelf eye-tracker. One non-limiting example is the Tobii Eye Tracker 4C™ or other products, sold by Tobii Group™ headquartered in Sweden Such eye-trackers are most popular for gaming applications, in which the eye-tracking device will display the current location of the user's gaze on the display. This allows the user to look at an object on the display and press a button or key to perform an action on the object (e.g., to select or shoot the object). Such eye-trackers may also be used to navigate within the game (e.g., to move in different directions) without manual interaction.

Software development kits (SDKs) are also available for such eye-tracking devices. These SDKs enable developers to develop software that utilizes the outputs of an eye-tracking device to dynamically detect a user's gaze point on the display, a distance between the display and each of the user's eyes, and a position or orientation of the user's head. Such information can be interpreted by software to identify gaze "gestures" performed by the user, and respond to those identified gestures. In addition, some operating systems (e.g., Windows™ 10) have integrated eye-tracking software that assists users with disabilities in using mouse and keyboard functions without having to operate a physical mouse or keyboard. However, no similar functionality has yet been provided for the viewing of digital slide images in digital pathology.

2. Process Overview

Embodiments of processes for utilizing an eye-tracking device 190 to review digital slide images will now be described in detail. It should be understood that the described processes may be embodied in one or more software modules that are executed by one or more hardware processors (e.g., processor 110). The described processes may be implemented as instructions represented in source code, object code, and/or machine code. These instructions may be executed directly by the hardware processor(s) 110, or alternatively, may be executed by a virtual machine operating between the object code and the hardware processor(s) 110.

Alternatively, the described processes may be implemented as a hardware component (e.g., general-purpose processor, integrated circuit (IC), application-specific integrated circuit (ASIC), digital signal processor (DSP), field-programmable gate array (FPGA) or other programmable logic device, discrete gate or transistor logic, etc.), combination of hardware components, or combination of hardware and software components. To clearly illustrate the interchangeability of hardware and software, various illustrative components, blocks, modules, circuits, and steps are described herein generally in terms of their functionality Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

Figure 2:
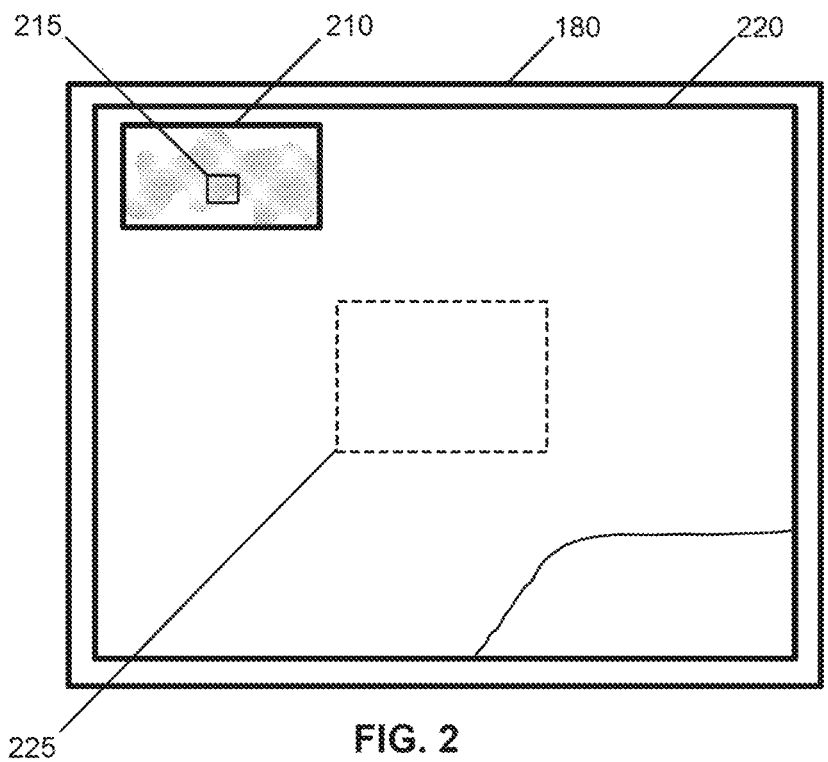
FIG. 2 illustrates an example display with a thumbnail image and macro view of a digital slide image, according to an embodiment.

The processes will be described with reference to the example display 180 in FIG. 2. FIG. 2 illustrates an example display 180 with a thumbnail image 215 of the digital slide image and a macro view 220 of the digital slide image, according to an embodiment. Thumbnail image 215, which is a small, low-resolution version of the entire digital slide image, comprises a frame 215 which highlights the region of interest currently being viewed, at a higher magnification, in macro view 220. In the illustrated embodiment, thumbnail image 215 is overlaid on macro view 220. However, in an alternative embodiment thumbnail image 215 may positioned on a side of macro view 220 or may be omitted entirely.

The graphical user interface in display 180 could comprise additional regions and components than those shown in FIG. 2. For example, display 180 could also comprise an intermediate view that shows the region of interest and/or an area surrounding the region of interest at an intermediate magnification that is higher than the magnification of thumbnail image 215 but lower than the magnification of macro view 220. In addition, the graphical user interface could comprise inputs for managing the view (e.g., zooming in or out, panning left, right, up, down, and/or along diagonals, customizing the view to a user's preference, etc.), using image processing tools (e.g., to analyze the content of the digital slide image, such as identifying and/or counting objects, etc.), and/or the like.

2.1. Panning

FIGS. 3A and 3B illustrate example processes for panning a digital slide image using the output of eye-tracking device 190, according to embodiments. While each of processes 300A and 300B is illustrated with a certain arrangement and ordering of steps, each process 300A and 300B may be implemented with fewer, more, or different steps and a different arrangement and/or ordering of steps. In addition, processes 300A and 300B may both be implemented in the same system 100 as a pair of alternative functions that can both be used by the user. Alternatively, only one of processes 300A and 300B may be implemented in any particular system 100. In any case, processes 300A and 300B may be executed by one or more processors 110.

In process 300A, the position of the user's gaze on display 180 is repeatedly detected in step 305A using eye-tracking device 190. Specifically, processor 110 may repeatedly receive an output of eye-tracking device 190 at regular time intervals (e.g., on the order of milliseconds) and/or whenever eye-tracking device 190 detects a change in the user's gaze. Each time processor 110 receives this output from eye-tracking device 190, processor 110 may determine the position of the user's gaze with respect to display 180 based on the received output.

In step 310, processor 110 correlates the position of the user's gaze, detected in step 305A, to a position within the graphical user interface currently being displayed on display 180. In an embodiment that utilizes thumbnail image 210, in step 310, processor 110 determines whether the user's gaze position within the current graphical user interface is within thumbnail image 210 or macro view 220. If the user's gaze position is within macro view 220 (i.e., "macro view" in step 310), process 300A proceeds to step 315. Otherwise, if the user's gaze position is within thumbnail image 210 (i.e., "thumbnail" in step 310), process 300A proceeds to step 330. In an embodiment in which the graphical user interface comprises more than a thumbnail image 210 and macro view 220, the user's gaze position may be outside both thumbnail image 210 and macro view 220. In this case (i.e., "neither" in step 310), process 300A returns to step 305A.

In step 315, processor 110 determines whether the current position of the user's gaze, detected in step 305A, has changed from a prior position of the user's gaze. For example, processor 110 may store one or more past positions of the user's gaze in memory (e.g., main memory 115 or secondary memory 120), and compare the current position of the user's gaze to the most recent past position of the user's gaze to determine whether or not the current position is different from the most recent past position. In addition, processor 110 may calculate a distance between the current position and past position and determine whether or not the distance is greater than a threshold value. The threshold value may be a non-zero distance value or, in one implementation, may simply be zero. If the threshold value is zero, processor 110 simply needs to determine whether or not the current position is different from the past position. In any case, if the change in position is greater than the threshold value (i.e., "Yes" in step 315), process 300A proceeds to step 320. Otherwise, if the change in position is not greater than the threshold value (i.e., "No" in step 315), process 300A returns to step 305A. In other words, panning will not occur until the user's gaze moves a distance greater than a predetermined threshold value, and will occur whenever the user's gaze moves a distance greater than the predetermined threshold value. In the event that the predetermined threshold value is zero, the panning will occur anytime the user's gaze moves.

In an alternative embodiment of step 315, processor 110 may determine whether or not the current position of the user's gaze is outside a region 225 within macro view 220. Region 225 encompasses an area around a center of macro view 220 that is smaller than the entire area of macro view 220. It should be understood that the position of region 225 is fixed with respect to display 180, such that the position of region 225 never changes even when panning occurs within macro view 220. While illustrated as a rectangle, region 225 could instead be a square, circle (e.g., defined by a radius), or other shape. If the user's gaze position, detected in step 305A, is within region 225 (e.g., analogous to "No" in step 315), process 300A may return to step 305A. Otherwise, if the user's gaze position, detected in step 305A, is outside region 225 (e.g., analogous to "Yes" in step 315), process 300A may proceed to step 320. In other words, panning will not occur as long as the user's gaze remains within region 225, and will occur whenever the user's gaze moves outside of region 225.

In step 320, processor 110 correlates the current position of the user's gaze on display 180 to a position on the portion of the digital slide image currently being viewed in macro view 220. For example, processor 110 may correlate the current position of the user's gaze on display 180 to a position on macro view 220 within the graphical user interface, and then correlate this position on macro view 220 to a position on the underlying digital slide image.

In step 325, processor 110 pans the underlying digital slide image to center the position on the digital slide image, determined in step 320, within macro view 220. In other words, macro view 220 is updated to consist of a region of interest of the digital slide image with the position, determined in step 320, centered within macro view 220. In updating macro image 220, processor 110 may automatically virtually "slide" the digital slide image to re-center the new position within macro view 220. Thus, the user can view the digital slide image being panned as the position on the digital slide image, determined in step 320, is moved into the center of macro view 220. In an embodiment, the velocity of the panning may be a function of the distance between the new position and the old position on the digital slide image that was previously centered within macro view 220 (i.e., the distance needed to be panned). For example, whenever performing the panning in step 325, processor 110 may calculate this panning distance, and pan the digital slide image within macro view 220 at a higher speed for longer distances and a lower speed for shorter distances. Once macro view 220 has been re-centered on the new position, process 300A returns to step 305A.

In step 330, processor 110 correlates the current position of the user's gaze on display 180 to a position on thumbnail image 210. In addition, processor 110 correlates the position on thumbnail image 210 to a position on the underlying digital slide image being viewed in macro view 220.

In step 335, processor 110 pans the underlying digital slide image to center the position on the digital slide image, determined in step 330, within macro view 220. In other words, the user may gaze at a position on thumbnail image 210 to select a region of interest, and processor 110 may automatically center macro view 220 on that region of interest, so that the user may view the region of interest at higher magnification. Step 335 may be identical or similar to step 325 described above. Once macro view 220 has been re-centered on the new position, process 300A returns to step 305A. It should be understood that, whenever a new region of interest is selected in this manner, processor 110 updates frame 215 to highlight the new region of interest within thumbnail image 210.

In process 300B, the position of the user's gaze on display 180 is repeatedly detected in step 305B using eye-tracking device 190. Step 305B may be identical or similar to step 305A described above. In addition to a user's gaze, the orientation of a user's head may also be detected in step 305B. For instance, the orientation of the user's head may be determined based on a direction of the user's gaze, as determined by the user's gaze position on display 180, or by other means (e.g., object recognition on the user's head). Regardless of how it is detected, processor 110 may compare a current orientation of the user's head to one or more past orientations of the user's head to identify head-based gestures (e.g., an upward tilting movement, a downward tilting movement, a head nod, a head shake, etc.).

In step 350, processor 110 determines whether or not a predetermined starting gesture has been detected. The predetermined starting gesture may comprise a head gesture that has been predefined for starting a pan across the digital slide image. As an example, the starting gesture may be a head nod (e.g., a movement of the head down, a movement of the head up, or a movement of the head down and up for at least a predefined number of times or for a predefined time period). However, other starting gestures are contemplated as well (e.g., a head shake, for example, from side to side). Regardless of the particular starting gesture that is used, if the starting gesture is detected (i.e., "Yes" in step 350), process 300B proceeds to step 355, in which detection of the starting gesture is used as an indication to start panning in a direction towards the user's current gaze position. Otherwise, if the particular starting gesture is not detected (i.e., "No" in step 350), process 300B returns to step 305B.

In step 355, processor 110 determines a direction from the center of macro view 220 to the current position of the user's gaze on display 180. Then, in step 360, processor 110 starts panning the digital slide image within macro view 220 according to the direction determined in step 355. For example, if the current position of the user's gaze is determined to be to the right of the center of macro view 220, processor 110 may start shifting the digital slide image within macro view 220 in the opposite direction (i.e., to the left), so as to move the current position of the user's gaze towards the center of macro view 220.

In step 365, processor 110 determines whether or not a predetermined stopping gesture has been detected. The predetermined stopping gesture may comprise a head gesture that has been predefined for stopping a pan across the digital slide image. In an embodiment, the stopping gesture may be identical to the starting gesture detected in step 350 (e.g., a head nod). Alternatively, the stopping gesture may be different from the starting gesture. If the stopping gesture is detected (i.e., "Yes" in step 365), process 300B proceeds to step 370. Otherwise, if the particular stopping gesture is not detected (i.e., "No" in step 365), process 300B returns to step 355.

In an embodiment, processor 110 may continue to monitor the current position of the user's gaze on display 180 throughout steps 355-365, in the same manner as in step 305B. In addition, processor 110 may continually update the direction of the panning in steps 355 and 360 as the current position of the user's gaze changes. Thus, the user may pan in any direction and change the direction of panning in real time by changing his or her gaze position. For example, if the initial position of the user's gaze is determined to be to the right of the center of macro view 220, processor 110 may start shifting the digital slide image within macro view 220 in the opposite direction (i.e., to the left), so as to move the current position of the user's gaze position towards the center of macro view 220. If the user subsequently moves his or her gaze upward within macro view 220, such that the user's gaze position is now above and to the right of the center of macro view 220 along a diagonal axis through the center of macro view 220, processor 110 may detect this change in gaze position and responsively start shifting the digital slide image within macro view 220 in the opposite direction along the diagonal axis, so as to move the current position of the user's gaze towards the center of macro view 220. It should be understood that the panning may continue continuously and comprise any number of direction changes until the stopping gesture is detected in step 365.

In step 370, in response to the detection of the stopping gesture in step 365, processor 110 stops the panning process within macro view 220. In other words, the digital slide image stops scrolling within macro view 220 and macro view 220 returns to being stationary. Then, process 300B returns to step 305B. Advantageously, process 300B can eliminate or reduce unwanted panning that may occur in process 300A (e.g., when a user temporarily shifts his or her gaze to a position outside of region 225 without intending to pan to that position).

2.2. Zooming and Other Functions

Figure 4A:
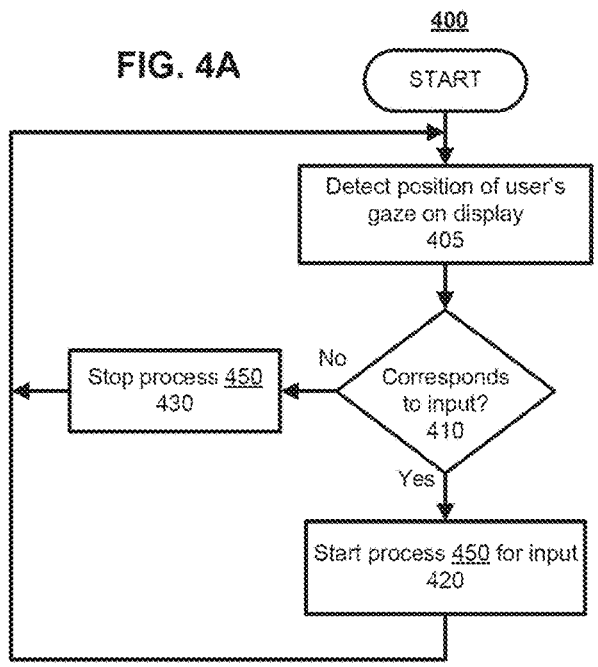
FIGS. 4A-4C illustrate example processes for performing image-viewing functions, such as zooming, according to embodiments.
Figure 4B:
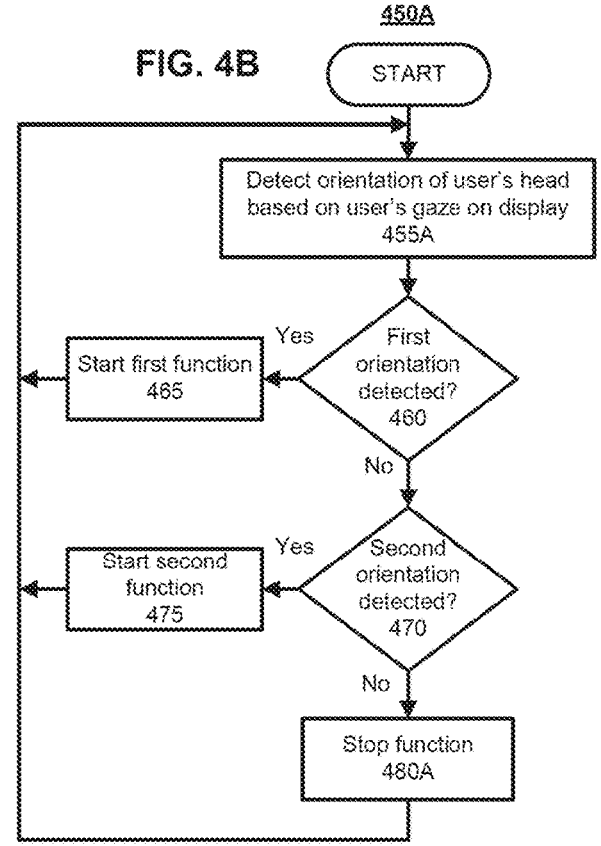
Figure 4C:
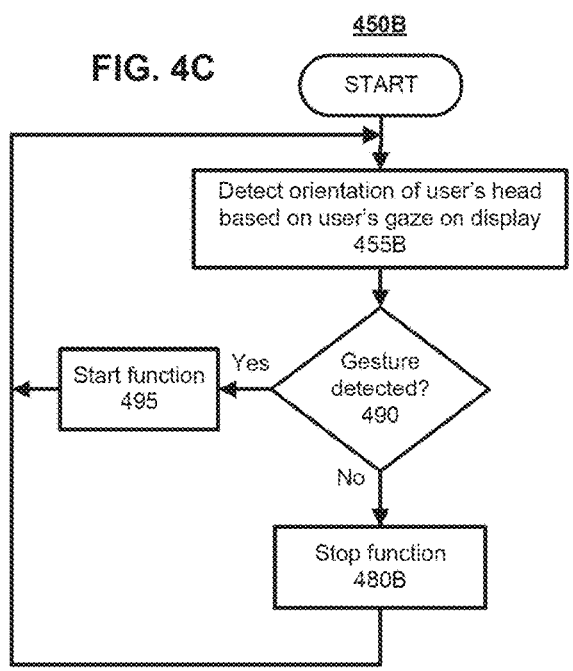

FIGS. 4A-4C illustrate example processes for performing image-viewing functions, such as zooming, according to embodiments. While each of processes 400 and 450 is illustrated with a certain arrangement and ordering of steps, each process 400 and 450 may be implemented with fewer, more, or different steps and a different arrangement and/or ordering of steps. Processes 400 and 450 may be executed by one or more processors 110.

In process 400, the position of the user's gaze on display 180 is repeatedly detected in step 405 using eye-tracking device 190. Step 405 may be identical or similar to steps 305A and 305B described with respect to FIGS. 3A and 3B, respectively.

In step 410, processor 110 determines whether or not the current position of the user's gaze, detected in step 405, corresponds to the position of an input within the graphical user interface currently being displayed on display 180. For example, processor 110 may correlate a position of the user's gaze on display 180 with a position on the graphical user interface and then determine whether or not that position on the graphical user interface is within the boundaries of an input (e.g., an icon, button, etc.) within the graphical user interface. If the current position of the user's gaze corresponds to an input (i.e., "Yes" in step 410), process 400 proceeds to step 420. Otherwise, if the current position of the user's gaze does not correspond to an input (i.e., "No" in step 410), process 400 proceeds to step 430.

In step 420, processor 110 identifies the input corresponding to the current position of the user's gaze and starts process 450 (e.g., either process 450A or 450B, depending on the embodiment or depending on the input) for that particular input. For example, the input may comprise a zoom button for changing a magnification of macro view 220. Alternatively, the input may comprise an input for performing a different binary function (e.g., changing a brightness of macro view 220) or non-binary function.

In step 430, processor 110 stops any process 450 that has been previously started for a particular input in step 420. If no process 450 is currently being executed for an input, step 430 is omitted. In either case, process 400 returns to step 405.

In process 450A, processor 110 detects the current orientation of the user's head in step 455A based on the user's gaze, as detected using eye-tracking device 190. For example, the orientation of the user's head may comprise an upward tilt, a downward tilt, a sideward tilt, and/or the like.

In step 460, processor 110 determines whether or not current orientation of the user's head matches a first orientation. For example, the first orientation may be a downward tilt. If the current orientation matches the first orientation (i.e., "Yes" in step 460), process 450A proceeds to step 465. In step 465, processor 110 starts a first function associated with the first orientation. For example, an association between the input, the first orientation, and the first function may be stored in memory (e.g., in a table in main memory 115 or secondary memory 120) in system 100. On the other hand, if the current orientation does not match the first orientation (i.e., "No" in step 460), process 450A proceeds to step 470.

In step 470, processor 110 determines whether or not the current orientation of the user's head matches a second orientation. For example, the second orientation may be an upward tilt. If the current orientation matches the second orientation (i.e., "Yes" in step 470), process 450A proceeds to step 475. In step 475, processor 110 starts a second function associated with the second orientation. For example, an association between the input, the second orientation, and the second function may be stored in memory (e.g., in a table in main memory 115 or secondary memory 120) in system 100. On the other hand, if the current orientation does not match the second orientation (i.e., "No" in step 470), process 450A proceeds to step 480A.

In step 480A, processor 110 stops any function that has been started in step 465 or step 475, and returns to step 455A. It should be understood that further orientations may be defined for any given input, and further functions may be associated with those orientations and that input. For example, steps 460 and 465 or steps 470 and 475 may be replicated for a third orientation (e.g., leftward tilt) associated with a third function, a fourth orientation (e.g., rightward tilt) associated with a fourth function, and so on and so forth.

As a concrete example of process 450A, the first orientation may comprise a downward tilt of the user's head and the first function may comprise zooming out (i.e., decreasing the magnification of macro view 220), and the second orientation may comprise an upward tilt of the user's head and the second function may comprise zooming in (i.e., increasing the magnification of macro view 220). Thus, the user may gaze at a zoom input within the graphical user interface and, while gazing at the zoom input, either tilt his or her head down to decrease the magnification of macro view 220 or up to increase the magnification of macro view 220. It should be understood that in an alternative embodiment, the first function may comprise zooming in, and the second function may comprise zooming out. In either case, the user may stop either zooming function by simply untilting his or her head or gazing outside of the zoom input.

In an embodiment, processor 110 may determine the speed at which the functions are performed based on the degree of an angle of the user's head orientation. Using the zoom example above, a greater downward tilt may result in processor 110 zooming out faster than for a smaller downward tilt, and a greater upward tilt may result in processor 110 zooming in faster than for a smaller upward tilt.

In an embodiment, at least one input may only be associated with only one possible function. For example, the graphical user interface may comprise separate inputs for zooming in and zooming out within macro view 220, separate inputs for panning left, right, up or down within macro view 220, and/or the like. In this case, process 450B may be used, instead of processor 450A, for the input.

In process 450B, processor 110 detects the current orientation of the user's head in step 455B based on the user's gaze as detected using eye-tracking device 190. Step 455B may be identical or similar to step 455A. In addition, processor 110 may compare a current orientation of the user's head to one or more past orientations of the user's head to identify head-based gestures (e.g., an upward tilt, downward tilt, a head nod, a head shake, etc.).

In step 490, processor 110 determines whether or not a predetermined gesture has been detected while the user is gazing at the input identified in step 410 of process 400. The predetermined gesture may comprise a head gesture that has been predefined for the input or in general for all inputs. As an example, the gesture may be a head nod (e.g., a movement of the head down, a movement of the head up, or a movement of the head down and up for at least a predefined number of times or for a predefined time period). However, other gestures are contemplated as well (e.g., a head shake). Regardless of the particular gesture that is used, if the gesture is detected (i.e., "Yes" in step 490), process 450B proceeds to step 495. In step 495, processor 110 starts a function associated with the input. On the other hand, if the particular gesture is not detected (i.e., "No" in step 490), process 450B proceeds to step 480B.

In step 480B, processor 110 stops any function that has been started in step 495, and returns to step 455B. Step 480B may be identical or similar to step 480A.

As a concrete example of process 450B, the input may be a button associated with a function of zooming in, zooming out, or selecting a preset magnification level, and the gesture may be a head nod. Thus, the user may gaze at the button within the graphical user interface, and, while gazing at the button, nod his or her head to perform the function associated with the button. In the event that the function is zooming in, processor 110 may increase the magnification of macro view 220 for as long as the user continues nodding and stop zooming in as soon as the user stops nodding. In the event that the function is zooming out, processor 110 may decrease the magnification of macro view 220 for as long as the user continues nodding and stop zooming out as soon as the user stops nodding In the event that the function is selecting a preset magnification level, processor 110 may change the magnification of macro view 220 to the preset magnification level as soon as the nod is detected, while further nodding may have no additional effect.

2.3. Gestures

A number of the processes described herein utilize gesture detection, based on a user's eye gaze, as detected by eye-tracking device 190. A plurality of gestures can be defined as independent combinations of outputs available from eye-tracking device 190. Eye-tracking device 190 may be configured to detect and output changes in head orientation along three axes (e.g., up and down tilt, left and right tilt, and left and right rotation). Notably, a person can look at the same point in a digital slide image independent of these three angles. Thus, eye-tracking device 190 may be able to detect and output changes in head orientation independent of the user's gaze position. In an embodiment, each gesture comprises a sequence of two or more simple and natural movements (e.g., an upward tilt, downward tilt, leftward tilt, rightward tilt, leftward rotation, rightward rotation, etc.) that is not confusingly similar to the sequences that define the other gestures. In other words, a plurality of unique sequences of basic movements, selected from a plurality of easily discernible basic movements, can be defined, with each unique sequence representing a different gesture.

2.4. Other Input Devices

It should be understood that the eye-tracking functions described herein may either be used to the exclusion of other input means or in conjunction with other input means. In an embodiment, in which the eye-tracking functions are used in conjunction with other input means, the eye-tracking functions provide an alternative to traditional inputs via hand-operated input devices, such as mice and keyboards. For example, in addition to using eye-tracking device 190 and its associated functions, the user may also utilize keyboard shortcuts and/or a mouse wheel for zooming in and out.

Thus, a user could gaze at a particular point on display 180 while pressing the keyboard shortcut or scrolling the mouse wheel to zoom in or out from that particular point. In this case, processor 110 may detect the location of the gaze point based on an output from eye-tracking device 190 and detect by how much to increase or decrease the magnification of the digital slide image based on an output from the keyboard or mouse. In this manner, the user utilizes the eye-tracking device 190 to replace some functions of the hand-operated input devices (e.g., navigating to or selecting a central point for zooming) but not all of the functions of the hand-operated input devices (e.g., zooming).

Accordingly, each particular user may decide how much to utilize or not utilize the eye-tracking functions implemented by the disclosed embodiments. This allows the users to tailor their usage of the eye-tracking functions to their own desires and comfort levels.

2.5. Analytics

In an embodiment, processor 110 and/or an external system (e.g., a remote server) may collect and store statistics related to how each user (e.g., pathologist) reviews each digital slide image. For example, each system 100 may collect and store gaze data, obtained from eye-tracking device 190, and periodically transmit this gaze data over one or more networks to a remote server for aggregation. The remote server may then utilize at least one processor of the remote server to analyze the aggregated gaze data collected from a plurality of systems 100.

The gaze data may comprise the areas of the digital slide images that were viewed by each pathologist, the dwell times for each area (i.e., how long each pathologist viewed the area), the order in which the areas were viewed by each pathologist, and/or the like. In an embodiment, aggregated gaze data may be used to train one or more machine-learning algorithms to understand how pathologists view or "parse" digital slide images. These trained machine-learning algorithms may then be used for other applications, such as predictive viewing. Predictive viewing may comprise predicting the area of a digital slide image that a pathologist will view next, based on the current area of the digital slide image being viewed and/or past areas of the digital slide image that were viewed by the pathologist. An image viewing application could then use this information to automatically retrieve and/or load the predicted next area of viewing into memory (e.g., loading the image data for the predicted next area from secondary memory 120 into main memory 115 for faster retrieval), automatically pan a view (e.g., macro view 220) of the digital slide image to the predicted next area of viewing, and/or the like.

A machine-learning algorithm for predictive viewing, as enabled by the disclosed embodiments, can replace the use of gestures for viewing digital slide images. The machine-learning algorithm can be trained on a particular user's viewing habits, so as to be able to predict the user's intentions while viewing a digital slide image. For example, the training dataset may comprise a history of the user's eye-tracking data, including the user's gaze positions and/or head orientations, along with the pixel data that was being viewed at those gaze positions and/or head orientations. The machine-learning algorithm may then be trained on this dataset to model the user's viewing habits, and predict where to pan and zoom next on a digital slide image. Thus, the trained machine-learning algorithm can drive the display to manage the user's viewing experience, so as to replace the need for processes 300, 400, and 450. For instance, based on past portions of a digital slide image that have been viewed by a user, the trained machine-learning algorithm may predict, in real time, a next portion of a digital slide image to be viewed, and processor 110 may automatically pan to that next portion (e.g., without any conscious gestures). Alternatively, processor 110 could suggest the next portion of the digital slide image to be viewed, and the user could either accept the suggestion, in which case processor 110 would pan to that next portion, or decline the suggestion, in which case processor 110 would not pan to that next portion.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

What is claimed is:

1. A system comprising:
   a computing device configured to sense a position of a user's gaze on a display; and
   at least one hardware processor configured to:
      detect the position of the user's gaze on the display, based on an output from the computing device, wherein the display displays at least a portion of an image within a macro view and a thumbnail image of the image;
      determine that the detected position of the user's gaze is within one of the thumbnail image or the macro view; and
      in response to determining that the detected position of the user's gaze is within one of the thumbnail image or the macro view,
         determine a position on the image that corresponds to the detected position within one of the thumbnail image or the macro view, and
         automatically update a view of the image within the macro view to move the position on the image that corresponds to the detected position within one of the thumbnail image or the macro view toward a center of the macro view.

2. The system of claim 1, wherein to automatically update the view of the image, the at least one hardware processor is further configured to automatically pan the view of the image.

3. The system of claim 1, wherein the at least one hardware processor is further configured to determine a modification of the position of the user's gaze from a first position to a second position, wherein the at least one hardware processor is further configured to automatically update the view of the image in response to determining the modification of the position of the user's gaze.

4. The system of claim 1, wherein the at least one hardware processor is further configured to determine a modification of the position of the user's gaze from a first position to a second position, wherein the at least one hardware processor is further configured to automatically update the view of the image to move a prior position away from the center of the macro view in response to determining the modification of the position of the user's gaze, wherein the prior position corresponds to the first position and the position corresponds to the second position.

5. The system of claim 1, wherein the at least one hardware processor is further configured to determine a modification of the position of the user's gaze from a first position to a second position, wherein the at least one hardware processor is further configured to automatically update the view of the image in response to determining the modification of the position of the user's gaze exceeds a threshold value.

6. The system of claim 1, wherein the image is obtained from a digital pathology slide server or scanning apparatus over a wired or wireless network.

7. The system of claim 1, wherein the thumbnail image is associated with a first image resolution and the macro view is associated with a second image resolution greater than the first image resolution.

8. The system of claim 1, wherein the thumbnail image is associated with a first magnification and the macro view is associated with a second magnification greater than the first magnification.

9. The system of claim 1, wherein the thumbnail image is overload on the macro view on the display.

10. The system of claim 1, wherein the at least one hardware processor is further configured to:
    determine a modification of the position of the user's gaze from a first position to a second position; and
    determine a speed of automatic updating based on the modification, wherein the at least one hardware processor is further configured to automatically update the view of the image based on the speed of automatic updating.

11. The system of claim 1, wherein the at least one hardware processor is further configured to:
    determine an orientation of a user's head based on the output from the computing device; and
    determine a starting gesture based on the orientation of the user's head, wherein the at least one hardware processor is further configured to automatically update the view of the image further in response to determining the starting gesture.

12. The system of claim 11, wherein the at least one hardware processor is further configured to:
    determine a stopping gesture based on the orientation of the user's head, and in response to determining the stopping gesture, automatically stop updating the view of the image.

13. A non-transitory computer-readable medium storing computer-executable instructions that, when executed by one or more computing devices, cause the one or more computing devices to:
   detect a position of a user's gaze on a display, wherein the display displays at least a portion of an image within a macro view and a thumbnail image of the image;
   determine that the detected position of the user's gaze is within one of the thumbnail image or the macro view; and
   in response to determining that the detected position of the user's gaze is within one of the thumbnail image or the macro view,
      determine a position on the image that corresponds to the detected position within one of the thumbnail image or the macro view, and
      automatically update a view of the image within the macro view to move the position on the image that corresponds to the detected position within one of the thumbnail image or the macro view toward a center of the macro view.

14. The non-transitory computer-readable medium of claim 13, the non-transitory computer-readable medium storing further computer-executable instructions that, when executed by the one or more computing devices, cause the one or more computing devices to:
   determine a modification of the position of the user's gaze from a first position to a second position; and
   automatically update the view of the image in response to determining the modification of the position of the user's gaze.

15. The non-transitory computer-readable medium of claim 13, the non-transitory computer-readable medium storing further computer-executable instructions that, when executed by the one or more computing devices, cause the one or more computing devices to:
   determine a modification of the position of the user's gaze from a first position to a second position; and
   automatically update the view of the image to move a prior position away from the center of the macro view in response to determining the modification of the position of the user's gaze, wherein the prior position corresponds to the first position and the position corresponds to the second position.

16. The non-transitory computer-readable medium of claim 13, the non-transitory computer-readable medium storing further computer-executable instructions that, when executed by the one or more computing devices, cause the one or more computing devices to:
   determine a modification of the position of the user's gaze from a first position to a second position; and
   automatically update the view of the image in response to determining the modification of the position of the user's gaze exceeds a threshold value.

17. The non-transitory computer-readable medium of claim 13, wherein the thumbnail image and the macro view are associated with at least one of different image resolutions or different magnifications.

18. The non-transitory computer-readable medium of claim 13, the non-transitory computer-readable medium storing further computer-executable instructions that, when executed by the one or more computing devices, cause the one or more computing devices to:
   determine an orientation of a user's head based on the output from the computing device;
   determine a starting gesture based on the orientation of the user's head;
   in response to determining the starting gesture, automatically update the view of the image;
   determine a stopping gesture based on the orientation of the user's head, and
   in response to determining the stopping gesture, automatically stop updating the view of the image.

19. A computer-implemented method comprising:
   detecting a position of a user's gaze on a display, wherein the display displays at least a portion of an image within a macro view and a thumbnail image of the image;
   determining that the detected position of the user's gaze is within one of the thumbnail image or the macro view; and
   in response to determining that the detected position of the user's gaze is within one of the thumbnail image or the macro view,
      determining a position on the image that corresponds to the detected position within one of the thumbnail image or the macro view, and
      automatically updating a view of the image within the macro view to move the position on the image that corresponds to the detected position within one of the thumbnail image or the macro view toward a center of the macro view.

20. The method of claim 19, further comprising determining a modification of the position of the user's gaze from a first position to a second position, wherein automatically updating the view of the image comprises automatically updating the view of the image in response to determining the modification of the position of the user's gaze.

* * * * *